United States Patent
Kirsch et al.

(10) Patent No.: US 6,875,894 B2
(45) Date of Patent: Apr. 5, 2005

(54) BIS(ALKYLTHIO)CARBENIUM SALTS

(75) Inventors: Peer Kirsch, Seeheim-Jugenheim (DE); Andreas Ruhl, Rossdorf (DE); Gerd-Volker Röschenthaler, Bremen (DE); Dmitrii Sevenard, Bremen (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/467,783

(22) PCT Filed: Feb. 11, 2002

(86) PCT No.: PCT/EP02/01401

§ 371 (c)(1), (2), (4) Date: Aug. 13, 2003

(87) PCT Pub. No.: WO02/064583

PCT Pub. Date: Aug. 22, 2002

(65) Prior Publication Data

US 2004/0063985 A1 Apr. 1, 2004

(51) Int. Cl.[7] .................. C07C 323/03; C07C 45/56; C07C 22/00; C07D 409/04; C07D 339/08

(52) U.S. Cl. .................. 568/38; 549/20; 549/21; 548/315.1; 568/57; 568/323; 568/664; 570/144

(58) Field of Search .................. 568/38, 57, 323, 568/664; 549/20, 21; 570/144; 548/315.1

(56) References Cited

U.S. PATENT DOCUMENTS 5,502,073 A    3/1996   Casida et al.

FOREIGN PATENT DOCUMENTS

DE    37 00 825 A      7/1987
EP    0 294 228 A A1   12/1988

OTHER PUBLICATIONS

CA:97:144807 abs of Liebigs Annalen der Chemie by Boehme et al (6) pp 1022–9 1982.*
CA:115:182590 abs of Liebigs Annalen der Chemie by Hartke et al (9) pp 903–16 1991.*
CA:139:260746 abs of Tetrahedron Letters by Sevenard et al 44(32) pp 5995–5998 2003.*
CA:124:86243 abs of Tetrahedron by Coustard J–M. 51(40) pp 10929 –40 1995.*
Cadamuro et al., *2–Substituted 1,3–benzoxathiolium* . . . , Synthesis, Bd. 7, 1987, Seiten 544–547, XP002206234.
Mocerino et al., *2–Phenyl–1, 3–benzhodithiolium trifluoromethansulfonate* . . . , Tetrahedron Lett., Bd. 31, Nr. 21, 1990, Seiten 3051–3054, XP001088235.
Kuroboshi et al., *Synthesis of perfluoroalkyl–substituted arenas* . . . , J. Fluorine Chem., Bd. 69, Nr. 2, 1994, Seiten 127–128, XP002206235.
Wang J.Q., et al.,*Asymmetric Total Synthesis of (+)–(3R, 4S, 5R, 7S)–Neoclausenamide*, Journal of the Chemical Society, Chemical Society, Letchworth, GB, Nr. 2, 1996, Seiten 209–212, XP000916286.
Okuyama, *Cyclic dithio–carbenium ion salts* . . . , Tetrahedron Lett., Bd. 23, Nr. 26, 1982, Seiten 2665–2666, XP001088236.
Sieber, *Modification of tryptophan* . . . , Tetrahedron Lett., Bd. 28, Nr. 15, 1987, Seiten 1637–1640, XP001087882.

* cited by examiner

Primary Examiner—Peter O'Sullivan
(74) Attorney, Agent, or Firm—Millen, White, Zelano & Branigan, P.C.

(57) ABSTRACT

The invention relates to bis(alkylthio)carbenium salts of the formula I

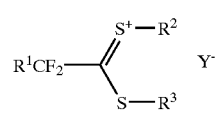

with the stated definitions for $R^1$, $R^2$, $R^3$ and $Y^-$, and to a process for the preparation thereof. The compounds according to the invention are advantageously suitable as electrophilic reagents for the transfer of fluorinated alkyl and acyl radicals onto nucleophilic compounds.

15 Claims, No Drawings

BIS(ALKYLTHIO)CARBENIUM SALTS

The invention relates to bis(alkylthio)carbenium salts as electrophilic reagents and to a process for the preparation thereof. The invention furthermore relates to uses of the bis(alkylthio)carbenium salts.

Compounds having one or more —$CF_2$— bridges, in particular having —$CF_2$—$CF_2$—, —$CF_2$—$CH_2$— or —$CF_2$—CO— bridges, can be used in particular as liquid crystals, but also as pharmaceuticals, crop-protection agents, such as insecticides, herbicides or fungicides, or for the preparation of polymers or as precursors of such products.

Compounds of this type are obtainable by one of the known processes by addition of a nucleophile onto an electrophilic perfluoroalkylating agent. L. M. Yagupolskii et al. (J. Org. Chem. USSR 1984, 20, 103) investigated (trifluoromethyl)diarylsulfonium salts as trifluoromethylating agents, but these did not give the desired reaction with the strongly activated aromatic system N,N-dimethylaniline. T. Umemoto and S. Ishihara (J. Am. Chem. Soc. 1993, 115, 2156–2164) describe S—, Se— and Te-(trifluoromethyl)-dibenzothio-, -seleno- and -tellurophenium salts as reactive electrophilic trifluoromethylating reagents. However, the said perfluoroalkylating agents have crucial disadvantages. Their area of application within which satisfactory selectivities and yields are achieved is limited. In addition, separation of the undesired secondary reaction products, for example from dibenzothiophene, is complex. Furthermore, they generally have a very high molecular weight in relation to the group to be transferred and can only be synthesised with considerable technical complexity and thus cannot be employed inexpensively on a commercial scale.

Starting from the stated prior art, it is an object of the present invention to indicate an electrophilic reagent which has a —$CF_2$— group in the α-position to the electrophilic carbon atom, is obtainable inexpensively from readily accessible starting materials and to which nucleophiles add under mild and technologically readily controllable reaction conditions, and compounds having at least one —$CF_2$—$CF_2$—, —$CF_2$—$CH_2$— or —$CF_2$—CO— bridge are accessible from the resultant addition products.

A further object of the present invention is to describe a process for the preparation of the electrophilic reagents according to the invention which starts from readily accessible starting materials, can also be employed on a commercial scale owing to technologically readily controllable reaction conditions, gives good yields and selectivities, and/or gives the electrophilic reagents in high purities.

A further object of the present invention is to indicate uses of the electrophilic reagents according to the invention, in particular processes for the preparation of compounds having one or more —$CF_2$—$CF_2$—, —$CF_2$—$CH_2$— and/or —$CF_2$—CO— bridges, which can be carried out under mild reaction conditions and on a commercial scale and/or give the desired products in good yields and selectivities.

The object is achieved by means of bis(alkylthio)carbenium salts of the formula I as electrophilic reagents according to claim 1. The sub-claims relate to advantageous embodiments of the invention.

The invention thus relates to bis(alkylthio)carbenium salts of the formula I

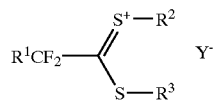

Above and below, $R^1$, $R^2$, $R^3$ and $Y^-$ have the following meanings:

$R^1$ is H, halogen, straight-chain, branched or cyclic alkyl having from 1 to 25 carbon atoms, in which one or more H atoms may be replaced by halogen, —CN or further optionally substituted alkyl and/or aryl radicals, and/or in which one or more non-adjacent —$CH_2$— groups may be replaced, independently of one another, by —CO—, —O—CO—, —CO—O—, —O—, —S—, -E-, —C≡C—, —NH— or —N($CH_3$)—, and/or aryl, which may be monosubstituted or polysubstituted by halogen, —CN or straight-chain, branched and/or cyclic alkyl and/or aryl, and in which one or more CH groups may be replaced by N, E is $CR^4$=$CR^5$ or $CHR^4$—$CHR^5$, $R^4$ and $R^5$ are each, independently of one another, H, alkyl having 1–6 carbon atoms, F, Cl, Br, $CF_3$ or CN, $R^2$ and $R^3$, independently of one another, are straight-chain, branched or cyclic alkyl having from 1 to 12 carbon atoms, where $R^2$ and $R^3$ may be bridged with one another in such a way that the

group is a 4- to 8-membered ring, and/or in which one or more H atoms may be replaced by halogen or further optionally substituted alkyl and/or aryl radicals, and/or in which one or more non-adjacent —$CH_2$— groups may be replaced, independently of one another, by —CO—, —O—, —S—, —CH=CH—, —C≡C—, —NH— or —N($CH_3$)—, and/or aryl, which may be monosubstituted or polysubstituted by halogen or straight-chain, branched and/or cyclic alkyl and/or aryl, and $Y^-$ is a non-coordinating or weakly coordinating anion.

With the bis(alkylthio)carbenium salts of the formula I according to the invention, novel electrophilic reagents are provided which have a —$CF_2$— group adjacent to the electrophilic carbon atom. A particular advantage of these reagents is their low molecolar weight in relation to the group to be transferred. Furthermore, these reagents can be synthesised inexpensively and can be employed under mild and technologically readily controllable reaction conditions.

Bis(alkylthio)carbenium salts in the form of dithianylium salts and the use thereof as alkylating agents for nucleophilic compounds are known (J. Nakayama, K. Fujiwara, M. Hoshino, Bull. Chem. Soc. Japan 1976, 49, 3567–3573, J. Klaveness, K. Undheim, Acta Chem. Scand. B, 1983, 37, 258–260, I. Stahl, Chem. Ber. 1985, 118, 1798–1808, I. Stahl, Chem. Ber. 1985, 118, 3159–3165, I. Stahl, Chem. Ber. 1987, 120, 135–139, M. Linker, G. Reuter, G. Frenzen, M. Maurer, J. Gosselck, I. Stahl, J. prakt. Chem. 1998, 340, 63–72). However, fluorinated bis(alkylthio)carbenium salts, in particular those of the formula I, are not disclosed in the literature. Their synthesis by the known processes does not result in the desired success owing to the extremely high electrophilicity. Even the use of the solvents usually used, such as aromatic hydrocarbons or nitrites, for example toluene or acetonitrile, generally causes decomposition of the bis(alkylthio)carbenium salts according to the invention.

The invention furthermore relates to a process for the preparation of the bis(alkylthio)carbenium salts of the formula I. In this process, a carboxylic acid or carboxylic acid derivative of the formula II

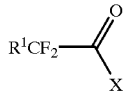

II is reacted with identical or different thiol compounds $R^2$—SH and $R^3$—SH, where the reaction is carried out in the presence of at least one acid HY and/or at least one acid HY, where Y⁻ is as defined above, is subsequently added to the reaction mixture.

Above and below,

X is OH, F, Cl, OR, $OSO_2$—R or OCO—$CF_2$—$R^1$, and

R is straight-chain, branched or cyclic alkyl having from 1 to 12 carbon atoms, in which one or more H atoms may be replaced by halogen, —CN or further optionally substituted alkyl and/or aryl radicals, and/or in which one or more non-adjacent —$CH_2$— groups may be replaced, independently of one another, by —CO—, —O—CO—, —CO—O—, —O—, —S—, —CH=CH—, —C≡C—, —NH— or —N($CH_3$)—, and/or aryl, which may be monosubstituted or polysubstituted by halogen, —CN or straight-chain, branched and/or cyclic alkyl and/or aryl, and in which one or more CH groups may be replaced by N.

This process according to the invention is distinguished by the fact that the carboxylic acid derivatives serving as starting materials are readily accessible, the reaction can be carried out under technologically readily controllable conditions, and the bis(alkylthio)carbenium salts are obtained in good yields and selectivities. This process can therefore be employed particularly advantageously for syntheses on a commercial scale.

The invention furthermore relates to the uses of the bis(alkylthio)carbenium salts of the formula I.

A first use relates to the preparation of compounds of the formula IV

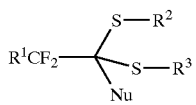

IV in which Nu is a nucleophilic radical, in which one or more bis(alkylthio)carbenium salts of the formula I are reacted with one or more nucleophilic compounds containing the nucleophilic radical Nu.

The compounds of the formula IV are interesting intermediates in the synthesis of compounds having at least one —$CF_2$-W-bridge, in which W denotes groups which are accessible by cleavage with simultaneous or subsequent functionalisation of the dithioketal group. The processes which can be employed for this purpose and the groups W themselves which are obtainable from the dithioketal group are known to the person skilled in the art. Examples of such groups W are —$CF_2$—, —$CH_2$— and —CO—, the syntheses of which are explained in greater detail in the following uses. In the bis(alkylthio)carbenium salts according to the invention, a reagent is thus provided for the transfer of fluorinated alkyl and acyl radicals, which may be optionally substituted, onto nucleophiles.

In the second use according to the invention of the bis(alkylthio)carbenium salts of the formula I, compounds of the formula V are obtained

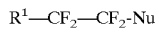

V

To this end, analogously to the above-mentioned first use, a compound of the formula IV is obtained by addition of a nucleophile onto a bis(alkylthio)carbenium salt and is subsequently subjected to oxidative fluoro-desulfuration by reaction with at least one fluorinating agent and at least one oxidant to give the compound of the formula V.

In the third use according to the invention of the bis(alkylthio)carbenium salts of the formula I, compounds of the formula VI are obtained

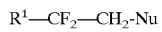

VI

Here too, the intermediate of the formula IV is firstly synthesised analogously to the first use mentioned. The compound of the formula IV is reduced by reaction with at least one reducing agent to give the compound of the formula VI.

The fourth use according to the invention of the bis(alkylthio)carbenium salts of the formula I relates to the preparation of compounds of the formula VII

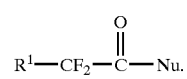

VII

In the first process step, a compound of the formula IV is prepared analogously to the uses mentioned above. This is subsequently hydrolysed to give the compound of the formula VII.

Owing to the stated advantages, in particular the ease of carrying out the process under mild reaction conditions, the bis(alkylthio)carbenium salts of the formula I according to the invention, the preparation process according to the invention and the uses described are particularly advantageously suitable for use in syntheses of liquid-crystalline compounds, pharmaceutical active ingredients, crop-protection agents, polymers and precursors thereof on a commercial scale.

Preferred variants and embodiments of the invention are explained in greater detail below.

As synthesis unit for liquid-crystalline compounds, $R^1$ preferably has the definition of the formula Ia

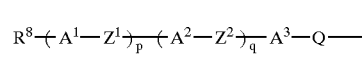

Ia in which $R^a$ is H, halogen, —CN, —NCS, —$SF_5$ or alkyl having from 1 to 18 carbon atoms, in which, in addition, one or two non-adjacent —$CH_2$— groups may be replaced by —O—, —S—, —CO—, —O—CO—, —CO—O—, -E- and/or —C≡C— and/or in which, in addition, one or more H atoms may be replaced by halogen and/or —CN, E is $CR^4$=$CR^5$ or $CHR^4$—$CHR^5$, $R^4$ and $R^5$ are each, independently of one another, H, alkyl having 1–6, carbon atoms, F, Cl, Br, $CF_3$ or CN, $Z^1$ and $Z^2$, independently of one another, are —O—CO—, —CO—O—, —$CH_2$—O—, —$CF_2$—O—, —O—$CH_2$—, —O—$CF_2$—, —$C_2H_4$—, —$CH_2$—$CF_2$—, —$CF_2$—$CH_2$—, —$CF_2$—$CF_2$—, —CH=CH—, —CF=CH—, —CH=CF—, —CF=CF—, —C≡C— or a single bond, $A^1$, $A^2$ and $A^3$ are each, independently of one another, 1,4-phenylene, in which one or more CH groups may be replaced by N, 1,4-cyclohexylene, in which one or two non-adjacent CH$_2$ groups may be replaced by O and/or S, 1,4-cyclohexenylene, 1,4-bicyclo[2.2.2]octylene, piperidine-1,4-diyl, naphthalene-2,6-diyl, decahydronaphthalene-2,6-diyl or 1,2,3,4-tetrahydronaphthalene-2,6-diyl, where, in the meanings given for A$^1$, A$^2$ and A$^3$, one or more H atoms may be substituted by halogen, in particular fluorine and/or chlorine, preferably fluorine, —CN and/or alkyl having from 1 to 6 carbon atoms, where one or more H atoms in the alkyl radical(s) may be replaced by halogen, in particular fluorine and/or chlorine, preferably fluorine, or —CN, and/or one or more non-adjacent —CH$_2$— groups may be replaced, independently of one another, by —CO—, —O—CO—, —CO—O—, —O—, —S—, —CH=CH—, —C≡C—, —NH— or —N(CH$_3$)—, and Q is —CH$_2$—, —CF$_2$—, —O—, —CO—, —O—CO—, —CO—O—, —C$_2$H$_4$—, —CH$_2$—CF$_2$—, —CF$_2$—CH$_2$—, —CF$_2$—CF$_2$—, —CH$_2$—O—, —CF$_2$—O—, —O—CH$_2$—, —O—CF$_2$—, —CH=CH—, —CF=CH—, —CH=CF—, —CF=CF—, —C≡C— or a single bond, p and q are 0, 1 or 2.

If a group or substituent, in particular Z$^1$, Z$^2$, A$^1$ or A$^2$, occurs more than once, it can in each case have identical or different meanings.

Above and below, the group E preferably has one of the following meanings: —C$_2$H$_4$—, —CH=CH—, —CF=CH—, —CH=CF—, —CF=CF—.

Particularly preferred meanings of R$^1$ in the above embodiment are indicated in the following formulae Ia1 to Ia3:

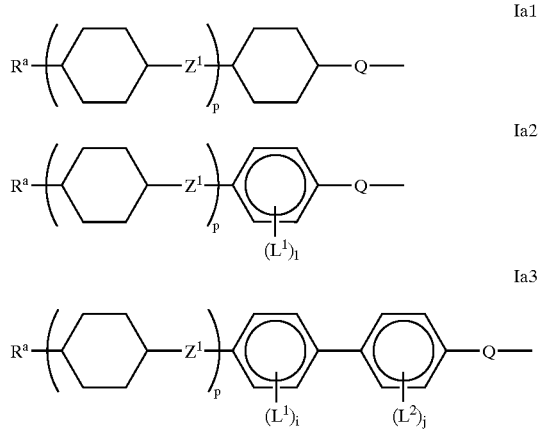

If A$^1$, A$^2$ and/or A$^3$ are cyclohexylene, these groups are preferably trans-substituted. Furthermore, one or two —CH$_2$— groups in the definition of these groups as cyclohexylene may be replaced by —O—, so that the following groups may also be present:

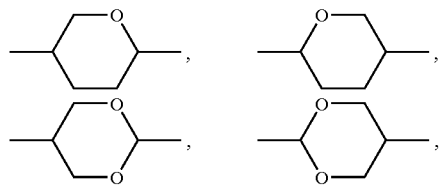

Above and below, L$^1$ and L$^2$, independently of one another, are F, Cl, or an alkyl, alkenyl, alkoxy and/or alkenyloxy group having from 1 to 6 carbon atoms, in which one or more H atoms may be substituted by fluorine, and i and j, independently of one another, are 0, 1, 2, 3 or 4, preferably 0, 1 or 2.

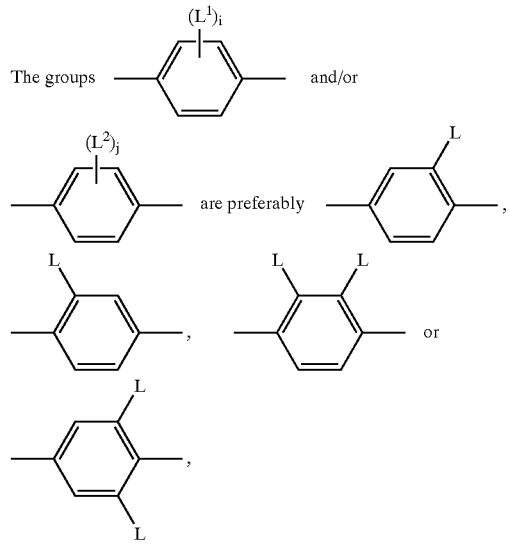

where L is as defined for L$^1$ and L$^2$, in particular is F.

In the case of the meaning alkyl in the groups or substituents indicated above or below, in particular in R$^a$, R$^1$, R$^2$ and/or R$^3$, the alkyl radical may be linear or branched. It preferably has 1, 2, 3, 4, 5, 6, 7 or 8 carbon atoms. It is preferably linear and is therefore particularly methyl, ethyl, propyl, butyl, pentyl, hexyl, heptyl or octyl. A branched alkyl radical may be chiral or achiral. Preferred chiral alkyl radicals are 2-butyl (=1-methylpropyl), 2-methylbutyl, 2-methylpentyl, 3-methylpentyl, 2-ethylhexyl, 2-propylpentyl and 2-octyl. Preferred achiral alkyl radicals are isopropyl, isobutyl (=methylpropyl) and isopentyl (=3-methylbutyl).

In the case of the meaning alkyl for R$^4$, R$^5$, R$^6$ and/or R$^7$, the alkyl radical is linear or branched. It is preferably linear and is therefore methyl, ethyl, propyl, butyl, pentyl or hexyl.

In the case of the meaning aryl for R$^1$, R$^2$ and/or R$^3$, the aryl radical is preferably phenyl or phenylene which is substituted in the para-position by straight-chain, branched and/or cyclic alkyl and/or aryl.

R$^1$ and R$^a$ are preferably alkyl, alkenyl, alkoxy, alkenyloxy, oxaalkyl or oxaalkenyl having from 1 to 8 carbon atoms.

Besides the above-mentioned meanings in the case of alkyl, R$^1$ and R$^a$ as alkyl may, in particular, also have more than 8 carbon atoms and are therefore particularly nonyl, decyl, undecyl, dodecyl, tridecyl, tetradecyl or pentadecyl.

Further preferred meanings of R$^1$ and R$^a$ are alkoxy. The alkoxy radical may be linear or branched. It is preferably linear and has 1, 2, 3, 4, 5, 6, 7 or 8 carbon atoms and is therefore particularly methoxy, ethoxy, propoxy, butoxy, pentoxy, hexoxy, heptoxy or octoxy, furthermore nonoxy, decoxy, undecoxy, dodecoxy, tridecoxy or tetradecoxy.

Furthermore, R$^1$ and R$^a$ are preferably oxaalkyl. The radical may be linear or branched. It is preferably linear and is, for example, 2-oxapropyl (=methoxymethyl), 2-(=ethoxymethyl) or 3-oxabutyl (=2-methoxyethyl), 2-, 3- or 4-oxapentyl, 2-, 3-, 4- or 5-okahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8- or 9-oxadecyl.

R$^1$ and R$^a$ may be a chiral or achiral group. Preferred chiral groups are 2-butyl (=1-methylpropyl), 2-methylbutyl, 2-methylpentyl, 3-methylpentyl, 2-ethylhexyl, 2-propylpentyl, 2-octyl, particularly 2-methylbutyl, 2-methylbutoxy, 2-methylpentoxy, 3-methylpentoxy, 2-ethylhexoxy, 1-methylhexoxy, 2-octyloxy, 2-oxa-3-methylbutyl, 3-oxa-4-methylpentyl, 4-methylhexyl, 2-nonyl, 2-decyl, 2-dodecyl, 6-methoxyoctoxy, 6-methyloctoxy, 6-methyloctanoyloxy, 5-methylheptyloxycarbonyl, 2-methylbutyryloxy, 3-methylvaleroyloxy, 4-methylhexanoyloxy, 2-methyl-3-oxapentyl, 2-methyl-3-oxahexyl, 1-methoxypropyl-2-oxy, 1-ethoxypropyl-2-oxy, 1-propoxypropyl-2-oxy, 1-butoxypropyl-2-oxy, 2-fluorooctyloxy and 2-fluorodecyloxy.

If $R^1$ and $R^a$ are an alkenyl radical, this may, be straight-chain or branched. It is preferably straight-chain and has from 2 to 8 carbon atoms. Accordingly, it is in particular vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, or oct-1-, -2-, -3-, -4-, -5-, -6- or -7-enyl.

If $R^1$ and $R^a$ are an alkenyloxy radical, this may be straight-chain or branched. It is preferably straight-chain and accordingly is in particular vinyloxy, prop-1- or -2-enyloxy, but-1-, -2- or -3-enyloxy, pent-1-, -2-, -3- or -4-enyloxy, hex-1-, -2-, -3-, -4- or -5-enyloxy, hept-1-, -2-, -3-, -4-, -5- or -6-enyloxy, or oct-1-, -2-, -3-, -4-, -5-, -6- or -7-enyloxy.

If $R^1$ and $R^a$ are an oxaalkenyl radical, this may be straight-chain or branched. It is preferably straight-chain and is particularly preferably 3-oxabut-1-enyl (=methoxyvinyl), 2-oxabut-3-enyl (=vinyloxymethyl), 4-oxapent-1-enyl (=methoxyprop-1-enyl), 3-oxapent-1-enyl (=ethoxyvinyl), 4-oxapent-2-enyl (=methoxyprop-2-enyl), 2-oxapent-3-enyl (=prop-1-enoxymethyl), 2-oxapent-4-enyl (=prop-2-enoxymethyl), 3-oxapent-4-enyl (=vinyloxyethyl), 3-oxahex-1-enyl, 4-oxahex-1-enyl, 5-oxahex-1-enyl, 4-oxahex-2-enyl, 5-oxahex-2-enyl, 2-oxahex-3-enyl, 5-oxahex-3-enyl, 2-oxahex-4-enyl, 3-oxahex-4-enyl, 2-oxahex-5-enyl, 3-oxahex-5-enyl or 4-oxahex-5-enyl.

In the above-mentioned meanings of $R^1$ and $R^a$ as alkyl, alkenyl, alkoxy, alkenyloxy, oxaalkyl or oxaalkenyl, one or more H atoms are preferably substituted by halogen atoms, preferably by fluorine and/or chlorine, particularly preferably by fluorine. Preferably, 2 or more H atoms are substituted by fluorine. Particularly preferably, 2 or 3H atoms in the terminal methyl group in the above-mentioned radicals are substituted by fluorine, so that the above-mentioned radicals contain a —$CHF_2$ or —$CF_3$-group. The entire radical $R^1$ or $R^a$ may also be perfluorinated.

Particularly preferred fluorinated radicals $R^1$ and $R^a$ as alkyl are —$CHF_2$, —$CF_3$, —$CH_2CHF_2$, —$CH_2CF_3$, —$CF_2CHF_2$, —$CF_2CF_3$, —$CH_2CH_2CHF_2$, —$CH_2CH_2CF_3$, —$CH_2CF_2CHF_2$, —$CH_2CF_2CF_3$, —$CF_2CH_2CHF_2$, —$CF_2CH_2CF_3$, —$CF_2CF_2CHF_2$, —$CF_2CF_2CF_3$, —$C_4F_9$, —$C_5F_{11}$, —$C_6F_{13}$, —$C_7F_{15}$ or —$C_8F_{17}$.

Particularly preferred fluorinated radicals $R^1$ and $R^a$ as alkenyl are —$CH=CHF$, —$CH=CF_2$, —$CF=CF_2$, —$CH=CHCF_3$, —$CH=CF—CF_3$, —$CF=CFCF_3$, —$CH_2—CH=CHF$, —$CH_2—CH=CF_2$, —$CF_2—CH=CH_2$, —$CF_2—CH=CHF$, —$CF_2—CH=CF_2$, —$CF_2—CF=CF_2$ or —$CF_2—CF=CFCF_3$.

Particularly preferred fluorinated radicals $R^1$ and $R^a$ as alkoxy are —$OCHF_2$, —$OCF_3$, —$OCH_2CHF_2$, —$OCH_2CF_3$, —$OCF_2CH_3$, —$OCF_2CHF_2$, —$OCF_2CF_3$, —$OCH_2CH_2CHF_2$, —$OCH_2CH_2CF_3$, —$OCH_2CF_2CHF_2$, —$OCH_2CF_2CF_3$, —$OCF_2CH_2CHF_2$, —$OCF_2CH_2CF_3$, —$OCF_2CF_2CHF_2$, —$OCF_2CF_2CF_3$, —$OCF_2CH_2CH_2CH_3$, —$OC_4F_9$, —$OCF_2CH_2CH_2CH_2CH_3$, —$OC_5F_{11}$, —$OCF_2(CH_2)_4CH_3$, —$OC_6F_{13}$, —$OC_7F_{15}$ or —$OC_8F_{17}$.

Particularly preferred fluorinated radicals $R^1$ and $R^a$ as alkenyloxy are —$OCH=CHF$, —$OCH=CF_2$, —$OCF=CF_2$, —$OCH=CHCF_3$, —$OCH=CF—CF_3$, —$OCF=CFCF_3$, —$OCH_2—CH=CHF$, —$OCH_2—CH=CF_2$, —$OCH_2—CF=CF_2$, —$OCF_2—CH=CH_2$, —$OCF_2—CH=CHF$, —$OCF_2—CH=CF_2$, —$OCF_2—CF=CF_2$, —$OCH_2—CH=CHCF_3$, —$OCF_2—CH=CHCH_3$, —$OCF_2—CH=CHCF_3$ or —$OCF_2—CF=CFCF_3$.

Particularly preferred fluorinated radicals $R^1$ and $R^a$ as oxaalkyl are —$CH_2OCHF_2$, —$CH_2OCF_3$, —$CF_2OCH_3$, —$CF_2OCHF_2$, —$CF_2OCF_3$, —$CH_2OCH_2CHF_2$, —$CH_2OCH_2CF_3$, —$CH_2OCF_2CF_3$, —$CF_2OCH_2CF_3$ or —$CF_2OCF_2CF_3$.

Particularly preferred fluorinated radicals $R^1$ and $R^a$ as oxaalkenyl are —$CH_2OCH=CHF$, —$CH_2OCH=CF_2$, —$CH_2OCF=CF_2$, —$CF_2OCH=CH_2$, —$CF_2OCH=CHF$, —$CF_2OCH=CF_2$, —$CF_2OCF=CF_2$, —$CH_2OCH=CHCF_3$, —$CH_2OCH=CFCF_3$, —$CH_2OCF=CFCF_3$, —$CF_2OCH=CHCH_3$, —$CF_2OCH=CHCF_3$, —$CF_2OCH=CFCF_3$ or —$CF_2OCF=CFCF_3$.

$R^1$ is very particularly preferably H, Hal, $Hal(CF_2)_k$—, $Hal(CF_2)_k$—O— or $Hal(CF_2)_k$—O—$CF_2$—, in which Hal is F, Cl, Br or I, and k can adopt a value of from 1 to 10.

The

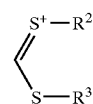

group is preferably in the form of a 4- to 8-membered ring of the formula

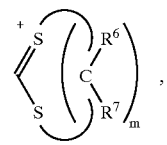

in which $R^6$ and $R^7$ are each, independently of one another, H or an optionally substituted alkyl or alkenyl group having from 1 to 6 carbon atoms, where the group

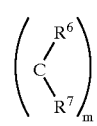

can form a cycloalkyl or aryl group, and m is 2, 3 or 4.

Particularly preferred meanings of the group

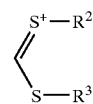

are therefore

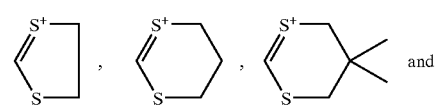 and

-continued

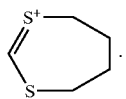

The counterion Y⁻ is a non-coordinating or weakly coordinating anion. Y⁻ here is preferably a halide, tetrafluoroborate, hexafluorophosphate, perchlorate or alkyl- or arylcarbonate or alkyl- or arylsulfonate anion, where one, a plurality or all H atoms in the alkyl or aryl groups may be substituted by fluorine or chlorine. Particularly preferred anions are trifluoromethanesulfonate and tetrafluoroborate.

Advantageous variants of the process according to the invention for the preparation of the bis(alkylthio)carbenium salts of the formula I are described below.

The reaction is preferably carried out with activated carboxylic acid derivatives, in particular with carboxylic acid chlorides, carboxylic acid fluorides, carboxylic anhydrides and carboxylic acid esters of sufficient activity.

The thiols used are preferably dithiols of the formula III

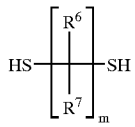

III in which R⁶, R⁷ and m are as defined above. Of these, particularly preferred dithiols are ethane-1,2-dithiol, propane-1,3-dithiol, 2,2-dimethylpropane-1,3-dithiol and butane-1,4-dithiol.

The dithiol compound is preferably employed in a molar ratio to the carboxylic acid or carboxylic acid derivative of from 0.8:1 to 1.6:1, particularly preferably in a ratio of about 1:1. If monothiol compounds are used instead of dithiols, twice the molar amount should be employed.

The reaction of the carboxylic acid or carboxylic acid derivative with the thiol compound is carried out in the presence of at least one acid HY and/or the acid HY is subsequently added to the reaction mixture. The anion Y⁻ has one of the meanings already indicated. The acid is advantageously trifluoromethanesulfonic acid and/or tetrafluoroboric acid, in particular in the form of the diethyl ether complex.

Based on the carboxylic acid or carboxylic acid derivative, the acid HY is advantageously employed in a molar ratio of from 0.8:1 to 3:1, in particular from 1:1 to 2:1.

The reaction time is selected, in particular, depending on the reactivity of the starting materials employed and the temperature set. In general, it is in the range from 30 minutes to 24 hours.

In order to shift the reaction equilibrium in the direction of the desired bis(alkylthio)carbenium salt of the formula I, it is advantageous to employ at least one water-binding agent. Examples of agents which are suitable for this purpose are anhydrides, such as acetic anhydride or trifluoroacetic anhydride.

The water-binding agent can be employed in a wide molar ratio, in particular from 0.8:1 to 10:1, based on the carboxylic acid or carboxylic acid derivative. The water-binding agent can be added to the reaction mixture simultaneously with the other starting materials. However, it is advantageously added after a reaction time, in particular after a reaction time of from 15 minutes to 12 hours.

Depending on the reactants used, it is not absolutely necessary to employ a solvent. If the product is not to be further reacted in situ, it is advantageous to precipitate it by addition of at least one suitable solvent. Suitable solvents or solvent mixtures for the reaction mixture and/or for precipitation of the product are those which do not react with the desired bis(alkylthio)carbenium salt (strong electrophile), in particular haloalkanes or ethers, for example dichloromethane, trichloromethane, diethyl ether, methyl tert-butyl ether or tetrahydrofuran.

The reaction is advantageously carried out at a temperature in the range from −80° C. to 70° C., in particular from −30 to 30° C.

The product in the form of a solid can be separated off and purified by conventional methods. To this end, the product is generally filtered off, washed with a suitable solvent or solvent mixture and/or purified by recrystallisation.

Advantageous and preferred variants of the uses according to the invention are described in greater detail below.

The nucleophilic compound which is added onto a bis (alkylthio)carbenium salt of the formula I preferably has a nucleophilic radical having at least one O, S, P, N or C atom as nucleophilic centre.

Nucleophiles having at least one nucleophilic O atom are, in particular, compounds having at least one hydroxyl group, particularly alkyl, aryl, alkylaryl and arylalkyl compounds having at least one hydroxyl, hydroperoxide and/or N-hydroxyl group.

Nucleophiles having at least one nucleophilic S atom are preferably thiols, thiophenols, sulfinic acid derivatives and thiophosphoric acid derivatives.

Compounds having at least one nucleophilic N atom are preferably amides, imides, heterocyclic compounds, such as imidazoles and triazoles, and azides, such as $N_3^-$ salts or $R_3SiN_3$, in which R is alkyl.

Suitable compounds having a nucleophilic P atom are, for example, trialkyl phosphites and phosphonic acid derivatives.

Nucleophiles having at least one nucleophilic C atom can in principle be all compounds having at least one aromatic group which are able to undergo electrophilic substitution. Further C-nucleophiles are CH-acidic compounds, such as, for example, β-dicarbonyl compounds and malonates, enolates, enol ethers, in particular trimethylsilylenol ethers, and enamines. In addition, organometallic compounds, such as, for example, organozinc, organocopper or organolithium compounds, Grignard reagents, organosilanes and 2-lithio-1,3-dithianes are all suitable C-nucleophiles.

For use in the synthesis of liquid-crystalline compounds, the nucleophilic radical advantageously contains structural units used in liquid-crystalline compounds.

The reaction conditions which are suitable for the reaction of the bis(alkylthio)carbenium salt with at least one nucleophile are known to the person skilled in the art from the standard literature on comparable reactions or can readily be derived therefrom (J. Nakayama, K. Fujiwara, M. Hoshino, Bull. Chem. Soc. Japan 1976, 49, 3567–3573; J. Klaveness, K. Undheim, Acta Chem. Scand. B, 1983, 37, 258–260; I. Stahl, Chem. Ber. 1985, 118, 1798–1808; I. Stahl, Chem. Ber. 1985, 118, 3159–3165; I. Stahl, Chem. Ber. 1987, 120, 135–139; M. Linker, G. Reuter, G. Frenzen, M. Maurer, J. Gosselck, I. Stahl, J. prakt. Chem. 1998, 340, 63–72; P. Kirsch, M. Bremer, A. Taugerbeck, T. Wallmichrath, Angew. Chem. 2001, 113, 1528–1532).

Thus, the reaction with the nucleophile is advantageously carried out in the presence of an auxiliary base (J. Nakayama in loco citato; P. Kirsch in loco citato). Suitable auxiliary bases are, in particular, organic amine compounds, for example triethylamine and/or pyridine.

In order to increase the nucleophilicity, it may also be advantageous firstly to convert the nucleophilic compound into an organometallic compound.

The resultant dithioketal compound of the formula IV is in turn a valuable synthetic unit, in which the dithioketal function can be further functionalised by known processes.

These further reactions are preferably carried out in situ, i.e. using the reaction mixture from the first step. However, it is also conceivable firstly to separate the compound of the formula IV off from the reaction mixture and, if necessary, to purify it.

Three preferred reactions of these are oxidative fluorodesulfuration, reduction and hydrolysis.

Oxidative fluorodesulfuration makes it possible to use the bis(alkylthio)carbenium salts according to the invention as fluoroalkylating agents, in the case of complete substitution by fluorine also as perfluoroalkylating agents. In particular in the case of aliphatic alcohols as nucleophiles, this opens up novel effective potential syntheses compared with the known processes which are afflicted with disadvantages.

The oxidative fluorodesulfuration is carried out using at least one oxidant and at least one fluorinating agent.

The oxidants used can be conventional oxidants. The oxidant employed is preferably a compound which liberates halonium equivalents. Examples of oxidants are N-bromosuccinimide, N-iodosuccinimide, 1,3-dibromo-5,5-dimethylhydantoin and bromine. Particular preference is given to bromine, since the resultant bromides can easily be separated off. Also suitable are, for example, $SO_2Cl_2$, $SO_2ClF$, nitrosonium and nitronium salts and chloramine T. The nitrosonium and nitronium salts can, if desired, also be prepared in situ from suitable precursors, for example from inorganic or organic nitrites and/or nitrates.

Fluorinating agents which can be employed are conventional fluorinating agents. The fluorinating agent is particularly preferably selected from the group formed by anhydrous hydrofluoric acid, aliphatic and aromatic amine/hydrogen fluoride complexes, such as, for example, pyridine/hydrogen fluoride complexes, in particular HF in pyridine having an HF content of from 50 to 70%, $NEt_3.3HF$, melamine/HF and polyvinyl-pyridine/HF.

The reaction with the oxidant and fluorinating agent is advantageously carried out at a temperature of from −100 to +50° C. Suitable solvents are the solvents and solvent mixtures indicated above.

With respect to the starting materials, solvents and reaction conditions which can be employed in the oxidative fluorodesulfuration, reference is made to the literature known, inter alia, for 1,3-dithianes and 1,3-dithiolanes, in particular to J. Kollonitsch, S. Marburg, L. M. Perkins, J. Org. Chem. 1976, 41, 3107–3111, S. C. Sondej, J. A. Katzenellenbogen, J. Org. Chem. 1986, 51, 3508–3513, G. K. S. Prakash, D. Hoole, V. P. Reddy, G. A. Olah, Synlett 1993, 691–698, R. D. Chambers, G. Sandford, M. Atherton, J. Chem. Soc. Chem. Commun. 1995, 177, R. D. Chambers, G. Sandford, M. E. Sparrowhawk, M. J. Atherton, J. Chem. Soc. Perkin Trans. 1, 1996, 1941–1944, C. York, G. K. S. Prakash, G. A. Olah, Tetrahedron 1996, 52, 9–14; M. Kuroboshi, T. Hiyama, J. Fluorine Chem. 1994, 69, 127–128 and P. Kirsch in loco citato.

Reduction of the dithioketal compound of the formula IV will enable a nucleophilic radical Nu to be coupled via a —$CF_2$—$CH_2$— bridge starting from the bis(alkylthio) carbenium salts of the formula I. In particular in the case of aliphatic alcohols, this represents an advantageous further potential synthesis compared with known processes.

Suitable reducing agents and the reaction conditions to be observed are known to the person skilled in the art from the literature from comparable reactions, for example from B.-T. Gröbel and D. Seebach, Synthesis 1977, 357–402, in particular 366, and from the literature cited therein. Merely by way of example, reaction with Raney nickel, for example by heating in ethanol, is mentioned here.

Hydrolysis of the dithioketal compound of the formula IV facilitates conversion into a —$CF_2$—CO— group, thus providing a fluoroacylating or perfluoroacylating agent with the bis(alkylthio)carbenium salts according to the invention via this synthetic route. Compared with known processes, this synthesis has the advantage of readily controllable and mild reaction conditions.

The suitable starting materials and reaction conditions are known to the person skilled in the art for the hydrolysis of 1,3-dithianes and 1,3-dithiolanes (B.-T. Gröbel and D. Seebach, Synthesis 1977, 357–402, in particular 359–365, and the literature cited therein). One possible hydrolysis is, for example, the reaction with N-bromosuccinimide and water, for example with acetone and/or tetrahydrofuran as solvent.

The following working example is intended to explain the invention without limiting it. Above and below, percentages are percent by weight. All temperatures are indicated in degrees Celsius.

WORKING EXAMPLES

1. Synthesis of 2-trifluoromethyl-1,3-dithianylium trifluoromethyl-sulfonate of the formula (1)

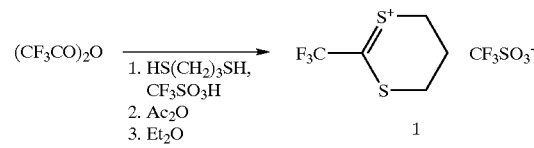

19 mmol of propane-1,3-dithiol were introduced into an apparatus which had been rendered inert and were cooled to 0° C., and 20 mmol of trifluoroacetic anhydride were then added dropwise with stirring. 29 mmol of trifluoromethane-sulfonic acid were then added dropwise at −10° C. over the course of 30 minutes, and the mixture was subsequently stirred at 0° C. for a further 2 hours. 76 mmol of acetic anhydride ($Ac_2O$) were then added dropwise at 0° C. over the course of 20 minutes, and the mixture was diluted with 30 ml of dry diethyl ether ($Et_2O$) and stirred for a further 5 minutes. The precipitate was filtered off and washed three times with 10 ml of diethyl ether each time.

The product is a colourless solid which was characterised as follows:

$^{19}$F-NMR (solvent mixture $CDCl_3$:$CH_3CN$ (3:2), 188 MHz, 20° C., standard: $CFCl_3$): δ=−64.3 (s, 3F), −79.9 (s, 3F);

$^1$H-NMR (solvent mixture $CDCl_3$:$CH_3CN$ (3:2), 200 MHz, 20° C.): δ=3.80 (t, 4H, $SCH_2$), 2.39–2.28 (mc, 2H, $CH_2CH_2CH_2$);

$^{13}$C-NMR (solvent mixture $CDCl_3$:$CH_3CN$ (3:2), 90 MHz, 303 K): δ=208.25 (quat, $J_{CF}$=36.2 Hz, —S—C=$S^+$—), 119.43 (quat, $J_{CF}$=319.0 Hz), 118.39 (quat, $J_{CF}$=283.05 Hz), 33.00 (s), 14.80 (s).

2. Conversion of 2-trifluoromethyl-1,3-dithianylium trifluoromethylsulfonate (1) into the dithioketal compound (2) and the further functionalisation thereof to the compounds (3), (4) and (5)

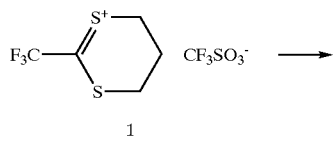

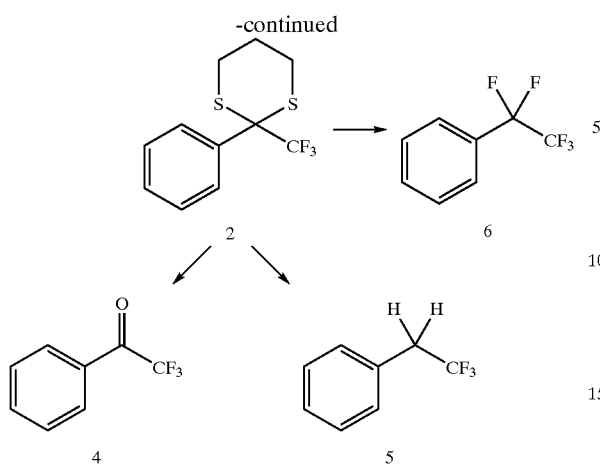

2.1 Preparation of the Dithioketal Compound of the Formula 2

0.1 mol of n-butyllithium (1.6 molar solution in diethyl ether) is added dropwise at −70° C. to 0.1 mol of bromobenzene in 500 ml of diethyl ether. After the mixture has been stirred at the same temperature for 30 minutes, 0.1 mol of anhydrous $ZnBr_2$ is added, the mixture is stirred for a further 30 minutes, and 0.1 mol of solid 2-trifluoromethyl-1,3-dithianylium trifluoromethylsulfonate (1) is introduced in portions. After the mixture has been warmed to about 20° C., 1 l of sodium chloride solution is added, the organic phase is separated off, and the aqueous phase is extracted a further twice with 100 ml of diethyl ether each time. The combined organic phases are washed with 200 ml of saturated sodium chloride solution and with 200 ml of water, dried over $MgSO_4$ and evaporated to dryness. The residue is chromatographed over silica gel in n-heptane/methyl tert-butyl ether 10:1, giving the dithioketal compound (2).

2.2 Oxidative Fluorodesulfuration of Compound (2) to Perfluoroethylbenzene (3)

Firstly, 200 mmol of 70% HF/pyridine and then in portions 50 mmol of solid N-iodosuccinimide are added at −70° C. to a solution of 20 mmol of the dithioketal (2) in 100 ml of dichloromethane. The mixture is stirred at −70° C. for 30 minutes and subsequently warmed to about 20° C. After 200 ml of water have been added and the mixture has been neutralised by addition of saturated $Na_2SO_3$ solution, the mixture is worked up in a conventional manner. The crude product is purified by chromatography over silica gel in n-heptane with subsequent distillation.

2.3 Hydrolysis of Compound (2) to Trifluoromethyl Phenyl Ketone (4)

Firstly, 30 mmol of water and then in portions 30 mmol of N-bromosuccinimide are added to a solution of 20 mmol of the dithioketal (2) in 100 ml of tetrahydrofuran. The mixture is subjected to conventional work-up. The product is purified by distillation.

2.4 Reduction of compound (2) to 2,2,2-trifluoroethylbenzene (5)

A solution of 10 mmol of the dithioketal (2) in 200 ml of ethanol is heated at the boil for 20 hours after addition of 20 g of Raney nickel. Filtration and conventional aqueous work-up as well as distillation of the product give compound (5).

3. Reaction of 2-trifluoromethyl-1,3-dithianylium trifluoromethylsulfonate (1) with (4'-propylbicyclohexyl-4-yl)methanol (6) and subsequent fluorodesulfuration

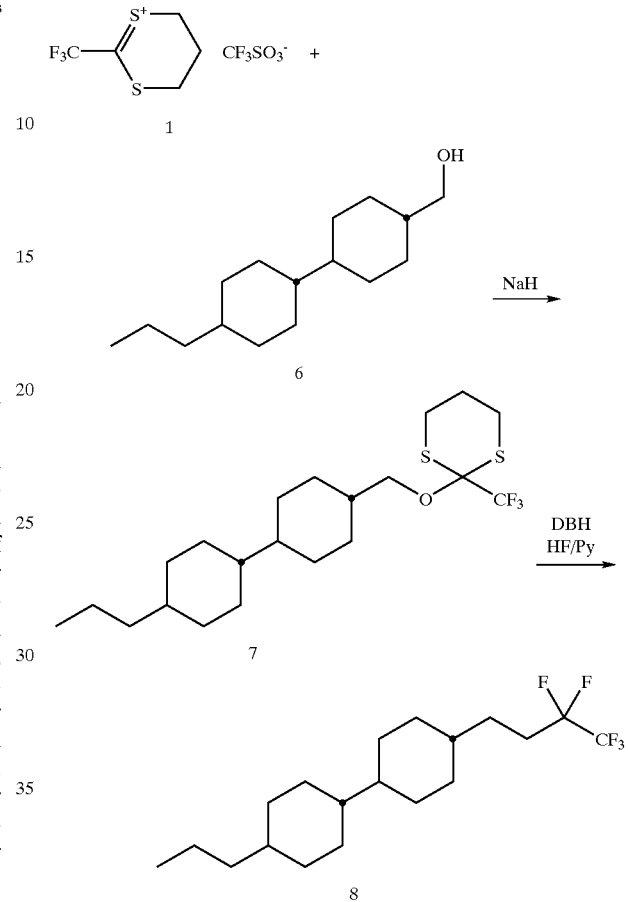

3.1 Synthesis of the Dithioorthoester (7)

4 mmol of NaH (as a 50% suspension in mineral oil) are added at 0° C. to a solution of 3 mmol of (4'-propylbicyclohexyl-4-yl)methanol (6) in 20 ml of dimethyl ether. The mixture is warmed to about 20° C., stirred for 1 hour and cooled to −35° C., and 3 mmol of the dithianylium salt (1) are added in portions. After the mixture has been stirred at this temperature for a further 1 hour, it is mixed with water (150 ml), and the resultant precipitate is filtered off, dried and slowly crystallised from hexane (150 ml). Product (7) is in the form of colourless crystals having a melting point of 70–72° C.

$^1$H NMR (CDCl$_3$, δ, ppm, J/Hz): 0.82–1.82 (m, 27H, CH$_3$, 10CH$_2$, 4CH); 1.88–2.01 (m, 2H, CH$_2$); 2.83–3.08 (m, 4H, 2S—CH$_2$); 3.61 (d, 2H, OCH$_2$, $^3J_{H-H}$=6.4).

$^{19}$F NMR (CDCl$_3$, δ, ppm): −78.89 s;

$^{13}$C NMR (CDCl$_3$, δ, ppm, J/Hz): 14.4 (s, CH$_3$); 20.0; 22.2; 27.5; 29.3; 30.0; 33.6; 39.8 (s, CH$_2$); 37.6; 38.0; 43.3; 43.4 (s, CH); 71.1 (s, OCH$_2$); 92.1 (q, $\underline{C}$CF$_3$, $^2J_{C-F}$=31.5); 124.5 (q, CF$_3$, $^1J_{C-F}$=284.5).

MS (178° C., m/e (%)): 424 (M$^+$, 55); 327 ([M-CF$_3$CO]$^+$, 17); 221 ([M-C$_5$H$_6$F$_3$S$_2$]$^+$, 97); 125 ([Pr-C$_6$H$_{10}$]$^+$, 85); 97 (CF$_3$CO$^+$, 100); 69 (CF$_3$$^+$, 97).

3.2 Fluorodesulfuration

A suspension of 2.5 mmol of dibromodimethylhydantoin in dry CH$_2$Cl$_2$ (2 ml) was introduced into an apparatus rendered inert with N$_2$, and HF/pyridine (70% solution having a content of 32 mmol of HF) is added at −70° C. The solution of 0.8 mmol of the dithianylium salt (7) is added dropwise to this mixture over the course of 20 minutes, and the mixture is then stirred at this temperature for a further 1 hour, slowly warmed to about 20° C. and stirred overnight. The solution is mixed with ice (100 g) and neutralised to pH=8 using an aqueous solution of NaOH×NaHCO$_3$× NaHSO$_3$. The mixture is extracted by shaking with CH$_2$Cl$_2$ (4×10 ml), and the organic phase is dried over MgSO$_4$. The solvent is stripped off under reduced pressure, and the residue is purified by column chromatography (eluent petroleum ether, silica gel). Product (8) (4-pentafluoroethoxymethyl-4'-propylbicyclohexane) is obtained as a colourless oil.

$^1$H NMR (CDCl$_3$, δ, ppm, J/Hz): 0.83–1.33 (m, 17H); 1.67–1.82 (m, 10H); 3.79 (d, 2H, OCH$_2$, $^3J_{H\text{-}H}$=6.4).

$^{19}$F NMR (CDCl$_3$, δ, ppm): −91.87 (s, 2F, OCF$_2$); −87.37 (s, 3F, CF$_3$).

$^{13}$C NMR (CDCl$_3$, δ, ppm, J/Hz): 14.4 (s, CH$_3$); 20.1; 29.2; 29.4; 30.1; 33.6; 39.8 (s, CH$_2$); 37.4; 37.6; 43.1; 43.3 (s, CH); 70.4 (t, OCH$_2$, $^3J_{C\text{-}F}$=4.5); 115.3 (t,q, CF$_2$, $^1J_{C\text{-}F}$=269.0, $^2J_{C\text{-}F}$=41.2); 116.8 (q, CF$_3$, $^1J_{C\text{-}F}$=284.4 $^2J_{C\text{-}F}$=45.7).

MS (200° C., m/e (%)): 356 (M$^+$, 30); 313 ([M-C$_3$H$_7$]$^+$, 3); 230 ([M-125-H]$^+$, 20); 125 ([Pr-C$_6$H$_{10}$]$^+$, 70); 119 (C$_2$F$_5^+$, 6); 69 (CF$_3^+$, 100); 41 (CH$_2$=CH—CH$_2^+$, 36); 29 (C$_2$H$_5^+$, 9).

4. Reaction of 2-trifluoromethyl-1,3-dithianylium trifluoromethylsulfonate (1) with 4-(4-propylcyclohexyl)phenol (9)

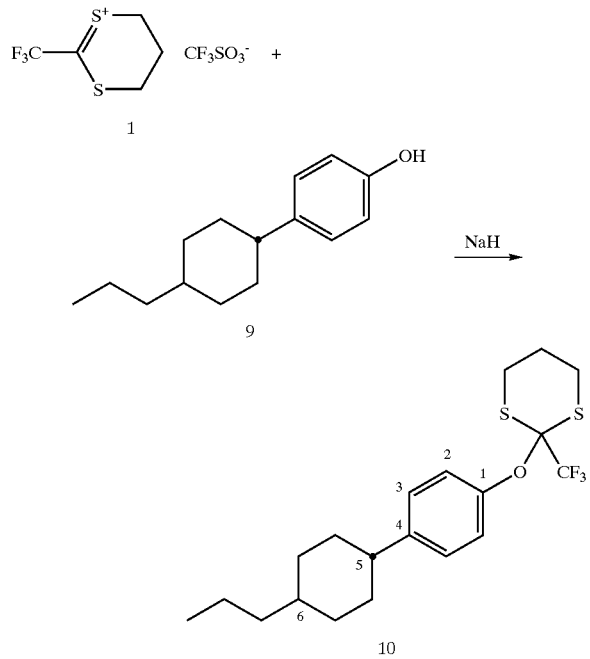

NaH (0.03 g of a 60% suspension in mineral oil, 0.8 mmol of NaH) is added at about 20° C. to a solution of 0.8 mmol of 4-(4-propylcyclohexyl)phenol (9) in 4 ml of tetrahydrofuran. The mixture is stirred for approximately 10 minutes and cooled to −55° C., and 0.8 mmol of the dithianylium salt (1) is added in portions. The mixture is then slowly warmed to about 20° C., mixed with 100 ml of water and extracted by shaking with CH$_2$Cl$_2$ (4×10 ml), and the organic phase is dried over MgSO$_4$. The solvent is stripped off under reduced pressure, and the residue is purified by column chromatography (eluent petroleum ether:CHCl$_3$ (1:1), silica gel). Product (10) is obtained as colourless crystals having a melting point of 120–128° C. (petroleum ether).

$^1$H NMR (CDCl$_3$, δ, ppm, J/Hz): 0.90 (t, 3H, CH$_3$, $^3J_{H\text{-}H}$=7.1); 0.97–1.55 (m, 9H); 1.74–1.97 (m, 6H); 2.38–2.61 (m, 3H); 2.79–2.92 (m, 2H); 7.13; 7.21 (AA'BB', 4H, C$_6$H$_4$, J$_{A\text{-}B}$=8.8).

$^{19}$F NMR (CDCl$_3$, δ, ppm): −79.81 s.

$^{13}$C NMR (CDCl$_3$, δ, ppm, J/Hz): 14.4 (s, CH$_3$); 20.0; 21.2; 27.1; 33.5; 34.4; 39.7 (s, CH$_2$); 37.0 (s, C$^6$, CH); 44.0 (s, C$^5$H); 96.2 (q, CCF$_3$, $^2J_{C\text{-}F}$=31.4); 124.3 (s, C$^4$); 124.5 (q, CF$_3$, $^1J_{C\text{-}F}$=283.4); 126.8–126.9 (m, C$^2$); 145.4 (s, C$^3$); 150.0 (s, C$^1$).

MS (EI, 115° C., m/e (%)): 404 (M$^+$, 0.2); 385 ([M-F]$^+$, 0.3); 187 (100).

5. Reaction of 2-trifluoromethyl-1,3-dithianylium trifluoromethylsulfonate (1) with 2-phenylimidazole (11)

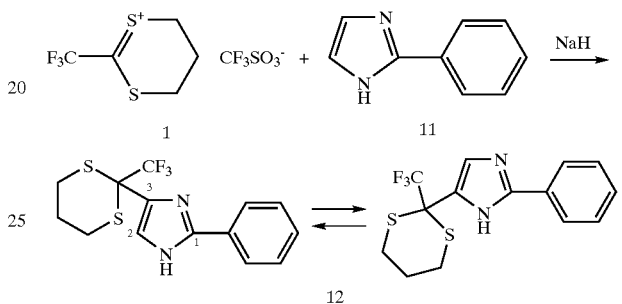

4 mmol of NaH (as a 60% suspension in mineral oil) are added at about 20° C. to a solution of 3 mmol of 2-phenylimidazole in 10 ml of tetrahydrofuran. The mixture is stirred for approximately 30 minutes and cooled to −70° C., and 3 mmol of the dithianylium salt (1) are added in portions. The mixture is then slowly warmed to −30° C., mixed with water (200 ml) and extracted by shaking with CH$_2$Cl$_2$ (4×15 ml), and the organic phase is dried over MgSO$_4$. The solvent is stripped off under reduced pressure, and the residue is purified by column chromatography (eluent petroleum ether:CHCl$_3$ (1:1), silica gel). The dithioorthoester (12) is obtained as a colourless oil.

$^1$H NMR (CDCl$_3$, δ, ppm): 1.73–2.00; 2.03; 2.21 (two m, each 1H, CH$_2$); 2.57–2.77 (m, 2H); 3.22 (m, 2H); 7.14–7.32 (m, 4H, C$_6$H$_4$+imidazole); 7.62–7.76 (m, 2H, C$_6$H$_5$).

$^{19}$F NMR (CDCl$_3$, δ, ppm): −69.75 s.

$^{13}$C NMR (CDCl$_3$, δ, ppm, J/Hz): 23.0 (s, CH$_2$); 28.0 (s, 2SCH$_2$); 51.6 (q, CCF$_3$, $^2J_{C\text{-}F}$=30.2), 119.5 (s, C$^2$); 125.9; 128.5; 128.8; 129.4 (s, C$_6$H$_5$); 126.8 (q, CF$_3$, $^1J_{C\text{-}F}$=283.3); 134.3 (s, C$^3$); 147.1 (s, C$^1$).

MS (186° C., m/e (%)): 330 (M$^+$, 100); 297 ([M-SH]$^+$, 35); 261 ([M-CF$_3$]$^+$, 47); 256 ([M-(CH$_2$)$_3$S]$^+$, 100); 187 ([M-(CH$_2$)$_3$S—CF$_3$]$^+$, 100); 77 (C$_6$H$_5^+$, 20).

The broadened signals, in particular in the $^{13}$C-NMR at 119.5 and 134.4 ppm, suggest the presence of the equilibrium mentioned.

What is claimed is:

1. A bis(alkylthio)carbenium salt of formula I

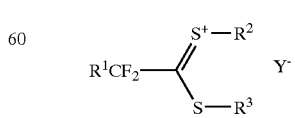

in which

R$^1$ is H, halogen, or a straight-chain, branched or cyclic alkyl having 1 to 25 carbon atoms, in which one or more H atoms are optionally replaced by halogen, —CN or by optionally substituted alkyl and/or aryl groups, and/or in which one or more non-adjacent —CH$_2$— groups are optionally replaced, independently of one another, by —CO—, —O—CO—, —CO—O—, —O—, —S—, -E-, —C≡C—, —NH— or —N(CH$_3$)—, and/or aryl, which are optionally monosubstituted or polysubstituted by halogen, —CN or straight-chain, branched and/or cyclic alkyl and/or aryl, and in which one or more CH groups are optionally replaced by N, E is CR$^4$=CR$^5$ or CHR$^4$—CHR$^5$, R$^4$ and R$^5$ are each, independently of one another, H, alkyl having 1–6 carbon atoms, F, Cl, Br, CF$_3$ or CN, R$^2$ and R$^3$ are, independently of one another, straight-chain, branched or cyclic alkyl having 1 to 12 carbon atoms, where R$^2$ and R$^3$ are optionally bridged with one another in such a way that the

group is a 5- to 8-membered ring, and/or in which one or more H atoms are optionally replaced by halogen or by an optionally substituted alkyl and/or aryl group, and/or in which one or more non-adjacent —CH$_2$— groups are optionally replaced, independently of one another, by —CO—, —O—, —S—, —CH=CH—, —C≡C—, —NH— or —N(CH$_3$)—, and/or aryl, which are optionally monosubstituted or polysubstituted by halogen or straight-chain, branched and/or cyclic alkyl and/or aryl, and Y$^-$ is a non-coordinating or weakly coordinating anion.

2. A bis(alkylthio)carbenium salt according to claim 1, wherein R$^1$ is H, Halogen, Halogen(CF$_2$)$_k$—, Halogen (CF$_2$)$_k$ —O— or Halogen(CF$_2$)$_k$—O—CF$_2$—, in which Halogen is F, Cl, Br or I, and k has a value of from 1 to 10.

3. A bis(alkylthio)carbenium salt of formula I

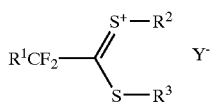

I wherein

R$^1$ is a group of the formula Ia

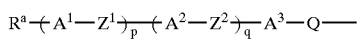

Ia in which

R$^a$ is H, halogen, —CN, —NCS, —SF$_5$ or alkyl having 1 to 18 carbon atoms, in which optionally one or two non-adjacent —CH$_2$— groups are replaced by —O—, —S—, —CO—, —O—CO—, —CO—O—, -E- and/or —C≡C— and/or in which optionally one or more H atoms are replaced by halogen and/or —CN, E is CR$^4$=CR$^5$ or CHR$^4$—CHR$^5$, R$^4$ and R$^5$ are each, independently of one another, H, alkyl having 1–6 carbon atoms, F, Cl, Br, CF$_3$ or CN, Z$^1$ and Z$^2$ are, independently of one another, —O—CO—, —CO—O—, —CH$_2$—O—, —CF$_2$—O—, —O—CH$_2$—, —O—CF$_2$—, —C$_2$H$_4$—, —CH$_2$—CF$_2$—, —CF$_2$—CH$_2$—, —CF$_2$—CF$_2$—, —CH=CH—, —CF=CH—, —CH=CF—, —CF=CF—, —C≡C— or a single bond,

A$^1$, A$^2$ and A$^3$ are each, independently of one another, 1,4-phenylene, in which one or more CH groups are optionally replaced by N, 1,4-cyclohexylene, in which one or two non-adjacent CH$_2$ groups are optionally replaced by O and/or S, 1,4-cyclohexenylene, 1,4-bicyclo[2.2.2]octylene, piperidine-1,4-diyl, naphthalene-2,6-diyl, decahydronaphthalene-2,6-diyl or 1,2,3,4-tetrahydronaphthalene-2,6-diyl, wherein in A$^1$, A$^2$ and A$^3$, one or more H atoms are optionally substituted by halogen, —CN and/or alkyl having 1 to 6 carbon atoms, in which one or more H atoms are optionally replaced by halogen or —CN, and/or in which one or more non-adjacent —CH$_2$— groups are optionally replaced, independently of one another, by —CO—, —O—CO—, —CO—O—, —O—, —S—, —CH=CH—, —C≡C—, —NH— or —N(CH$_3$)—, Q is —CH$_2$—, —CF$_2$—, —O—, —CO—, —O—CO—, —CO—O—, —C$_2$H$_4$—, —CH$_2$—CF$_2$—, —CF$_2$—CH$_2$—, —CF$_2$—CF$_2$—, —CH$_2$—O—, —CF$_2$—O—, —O—CH$_2$—, —O—CF$_2$—, —CH=CH—, —CF=CH—, —CH=CF—, —CF=CF—, —C≡C— or a single bond, p and q are, independently of one another, 0, 1 or 2, R$^2$ and R$^3$ are, independently of one another, straight-chain, branched or cyclic alkyl having 1 to 12 carbon atoms, where R$^2$ and R$^3$ are optionally bridged with one another in such a way that the

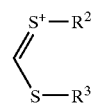

group is a 5- to 8-membered ring, and/or in which one or more H atoms are optionally replaced by halogen or by an optionally substituted alkyl and/or aryl group, and/or in which one or more non-adjacent —CH$_2$— groups are optionally replaced, independently of one another, by —CO—, —O—, —S—, —CH=CH—, —C≡C—, —NH— or —N(CH$_3$)—, and/or aryl, which are optionally monosubstituted or polysubstituted by halogen or straight-chain, branched and/or cyclic alkyl and/or aryl, and Y$^-$ is a non-coordinating or weakly coordinating anion.

4. A bis(alkylthio)carbenium salt according to claim 1, wherein the

group is a 5- to 8-membered ring of the formula

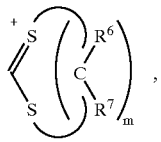

in which
$R^6$ and $R^7$ are each, independently of one another, H or an optionally substituted alkyl or alkenyl group having 1 to 6 carbon atoms, where the group

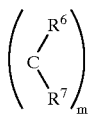

optionally, in each case independently, form a cycloalkyl or aryl group, and
m is 2, 3 or 4.

5. A bis(alkylthio)carbenium salt according to claim 1, wherein $Y^-$ is a halide, tetrafluoroborate, hexafluorophosphate, perchlorate, alkyl- or arylcarbonate anion or alkyl- or arylsulfonate anion,
where one or more H atoms in the alkyl or aryl groups are optionally substituted by fluorine or chlorine.

6. A process for preparing a bis(alkylthio)carbenium salt of formula I according to claim 1,

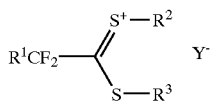

in which
$R^1$, $R^2$, $R^3$ and $Y^-$ are as defined in claim 1, comprising reacting a compound of formula II

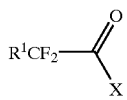

in which $R^1$ is as defined above, and
X is OH, F, Cl, OR, $OSO_2$—R or OCO—$CF_2$—$R^1$, and
R is a straight-chain, branched or cyclic alkyl having 1 to 12 carbon atoms,
in which one or more H atoms are optionally replaced by halogen, —CN or by an optionally substituted alkyl and/or aryl group, and/or
in which one or more non-adjacent —$CH_2$— groups are optionally replaced, independently of one another, by —CO—, —O—CO—, —CO—O—, —O—, —S—, —CH=CH—, —C≡C—, —NH— or —N($CH_3$)—, and/or aryl,
which are monosubstituted or polysubstituted by halogen, —CN or straight-chain, branched and/or cyclic alkyl and/or aryl, and
in which one or more CH groups are optionally replaced by N, with identical or different thiol compounds $R^2$—SH and $R^3$—SH, in which $R^2$ and $R^3$ are as defined above, where the reaction is carried out in the presence of an acid HY and/or the acid HY is added to the reaction mixture, where Y in HY is $Y^-$ which is as defined above.

7. A process according to claim 6, wherein the two thiol compounds $R^2$—SH and $R^3$—SH are bridged with one another and are jointly in the form of a dithiol compound of formula III

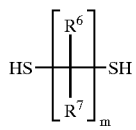

wherein
$R^6$ and $R^7$ are each, independently of one another, H or an optionally substituted alkyl or alkenyl group having 1 to 6 carbon atoms, and
m is 2, 3 or 4.

8. A process for preparing a compound of formula IV

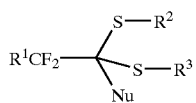

in which,
$R^1$ is H, halogen, or a straight-chain, branched or cyclic alkyl having 1 to 25 carbon atoms,
in which one or more H atoms are optionally replaced by halogen, —CN or by optionally substituted alkyl and/or aryl groups, and/or
in which one or more non-adjacent —$CH_2$— groups are optionally replaced, independently of one another, by —CO—, —O—CO—, —CO—O—, —O—, —S—, -E-, —C≡C—, —NH— or —N($CH_3$)—, and/or
aryl,
which are optionally monosubstituted or polysubstituted by halogen, —CN or straight-chain, branched and/or cyclic alkyl and/or aryl, and in which one or more CH groups are optionally replaced by N,
$R^2$ and $R^3$ are, independently of one another, straight-chain, branched or cyclic alkyl having 1 to 12 carbon atoms,
where $R^2$ and $R^3$ are optionally bridged with one another in such a way that the

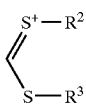

group is a 5- to 8-membered ring, and/or
in which one or more H atoms are optionally replaced by halogen or by an optionally substituted alkyl and/or aryl group, and/or
in which one or more non-adjacent —CH$_2$— groups are optionally replaced, independently of one another, by —CO—, —O—, —S—, —CH=CH—, —C≡C—, —NH— or —N(CH$_3$)—, and/or aryl, which are optionally monosubstituted or polysubstituted by halogen or straight-chain, branched and/or cyclic alkyl and/or aryl, and Nu is a nucleophilic group,
comprising reacting a bis(alkylthio)carbenium salt of formula I according to claim 1 with one or more nucleophilic compounds.

9. A method for preparing a compound of formula V

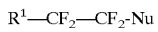

R$^1$—CF$_2$—CF$_2$-Nu                         V in which Nu, and R$^1$ are as defined below, comprising
a) reacting a bis(alkylthio)carbenium salt of formula I with a nucleophilic compound to give a compound of formula IV

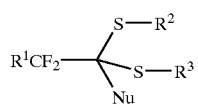

IV in which
R$^1$ is H, halogen, or a straight-chain, branched or cyclic alkyl having 1 to 25 carbon atoms,
in which one or more H atoms are optionally replaced by halogen, —CN or by optionally substituted alkyl and/or aryl groups, and/or
in which one or more non-adjacent —CH$_2$— groups are optionally replaced, independently of one another, by —CO—, —O—CO—, —CO—O—, —O—, —S—, -E-, —C≡C—, —NH— or —N(CH$_3$)—, and/or
aryl,
which are optionally monosubstituted or polysubstituted by halogen, —CN or straight-chain, branched and/or cyclic alkyl and/or aryl, and in which one or more CH groups are optionally replaced by N,
R$^2$ and R$^3$ are, independently of one another, straight-chain, branched or cyclic alkyl having 1 to 12 carbon atoms,
where R$^2$ and R$^3$ are optionally bridged with one another in such a way that the

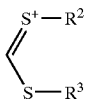

group is a 5- to 8-membered ring, and/or
in which one or more H atoms are optionally replaced by halogen or by an optionally substituted alkyl and/or aryl group, and/or
in which one or more non-adjacent —CH$_2$— groups are optionally replaced, independently of one another, by —CO—, —O—, —S—, —CH=CH—, —C≡C—, —NH— or —N(CH$_3$)—, and/or aryl, which are optionally monosubstituted or polysubstituted by halogen or straight-chain, branched and/or cyclic alkyl and/or aryl, and
Nu is a nucleophilic group, and
b) reacting the compound of formula IV with a fluorinating agent and an oxidant to give a compound of formula V.

10. A method for preparing a compound of formula VI

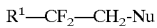

R$^1$—CF$_2$—CH$_2$-Nu                         VI in which Nu and R$^1$ is as defined below, comprising
a) reacting a bis(alkylthio)carbenium salt of formula I with a nucleophilic compound to give a compound of formula IV

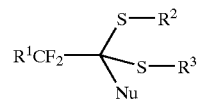

IV in which Nu is a nucleophilic group, and
R$^1$ is H, halogen, or a straight-chain, branched or cyclic alkyl having 1 to 25 carbon atoms,
in which one or more H atoms are optionally replaced by halogen, —CN or by optionally substituted alkyl and/or aryl groups, and/or
in which one or more non-adjacent —CH$_2$— groups are optionally replaced, independently of one another, by —CO—, —O—CO—, —CO—O—, —O—, —S—, -E-, —C≡C—, —NH— or —N(CH$_3$)—, and/or
aryl,
which are optionally monosubstituted or polysubstituted by halogen, —CN or straight-chain, branched and/or cyclic alkyl and/or aryl, and in which one or more CH groups are optionally replaced by N,
R$^2$ and R$^3$ are, independently of one another, straight-chain, branched or cyclic alkyl having 1 to 12 carbon atoms,
where R$^2$ and R$^3$ are optionally bridged with one another in such a way that the

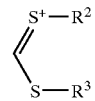

group is a 5- to 8-membered ring, and/or in which one or more H atoms are optionally replaced by halogen or by an optionally substituted alkyl and/or aryl group, and/or
in which one or more non-adjacent —CH$_2$— groups are optionally replaced, independently of one another, by —C—, —O—, —S—, —CH=CH—, —C≡C—, —NH— or —N(CH$_3$)—, and/or aryl, which are optionally monosubstituted or polysubstituted by halogen or straight-chain, branched and/or cyclic alkyl and/or aryl,
b) reacting the compound of formula IV with a reducing agent to give a compound of formula VI.

11. A method for preparing a compound of formula VII

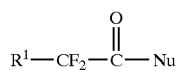  VII in which Nu and $R^1$ is as defined below, comprising
  a) reacting a bis(alkylthio)carbenium salt of formula I with a nucleophilic compound to give a compound of formula IV

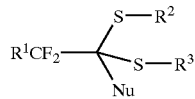  IV in which Nu is a nucleophilic group, and
  $R^1$ is H, halogen, or a straight-chain, branched or cyclic alkyl having 1 to 25 carbon atoms,
    in which one or more H atoms are optionally replaced by halogen, —CN or by optionally substituted alkyl and/or aryl groups, and/or
    in which one or more non-adjacent —CH$_2$— groups are optionally replaced, independently of one another, by —CO—, —O—CO—, —CO—O—, —O—, —S—, -E-, —C≡C—, —NH— or —N(CH$_3$)—, and/or
  aryl,
    which are optionally monosubstituted or polysubstituted by halogen, —CN or straight-chain, branched and/or cyclic alkyl and/or aryl, and in which one or more CH groups are optionally replaced by N,
  $R^2$ and $R^3$ are, independently of one another, straight-chain, branched or cyclic alkyl having 1 to 12 carbon atoms,
  where $R^2$ and $R^3$ are optionally bridged with one another in such a way that the

group is a 5- to 8-membered ring, and/or in which one or more H atoms are optionally replaced by halogen or by an optionally substituted alkyl and/or aryl group, and/or
    in which one or more non-adjacent —CH$_2$— groups are optionally replaced, independently of one another, by —CO—, —O—, —S—, —CH=CH—, —C≡C—, —NH— or —N(CH$_3$)—, and/or aryl,
      which are optionally monosubstituted or polysubstituted by halogen or straight-chain, branched and/or cyclic alkyl and/or aryl,
  b) hydrolysing the compound of formula IV to give a compound of formula VII.

12. A process according to claim 8, wherein Nu contains at least one O, S, P, N and/or C atom as nucleophilic centre.

13. A bis(alkylthio)carbenium salt according to claim 1, wherein $Y^-$ is a non-coordinating anion.

14. A bis(alkylthio)carbenium salt according to claim 3, wherein $Y^-$ is a non-coordinating anion.

15. A bis(alkylthio)carbenium salt according to claim 3, wherein $Y^-$ is a halide, tetrafluoroborate, hexafluorophosphate, perchlorate, alkyl- or arylcarbonate anion or alkyl- or arylsulfonate anion,
  where one or more H atoms in the alkyl or aryl groups are optionally substituted by fluorine or chlorine.

* * * * *

UNITED STATES PATENT AND TRADEMARK OFFICE
CERTIFICATE OF CORRECTION

PATENT NO. : 6,875,894 B2
DATED : April 5, 2005
INVENTOR(S) : Peer Kirsch et al.

It is certified that error appears in the above-identified patent and that said Letters Patent is hereby corrected as shown below:

Column 17,
Line 44, reads "value of from" should read -- value of --.

Column 22,
Line 61, reads "by –C–, –O–," should read -- by –CO–, –O–, --.

Signed and Sealed this

Fourteenth Day of March, 2006

JON W. DUDAS
*Director of the United States Patent and Trademark Office*

UNITED STATES PATENT AND TRADEMARK OFFICE
CERTIFICATE OF CORRECTION

PATENT NO. : 6,875,894 B2
APPLICATION NO. : 10/467783
DATED : April 5, 2005
INVENTOR(S) : Peer Kirsch et al.

It is certified that error appears in the above-identified patent and that said Letters Patent is hereby corrected as shown below:

<u>Title page,</u>
Insert Item -- [30] Foreign Application Priority Data
            Feb. 13, 2001 (DE)    101 06 577 --.

<u>Column 17,</u>
Line 44, reads "value of from" should read -- value of --.

<u>Column 22,</u>
Line 61, reads "by –C–, –O–," should read -- by –CO–, –O–, --.

Signed and Sealed this

Twentieth Day of June, 2006

JON W. DUDAS
*Director of the United States Patent and Trademark Office*